United States Patent [19]

Rossi et al.

[11] 4,399,292

[45] Aug. 16, 1983

[54] PROCESS FOR PURIFYING OXYGEN CONTAINING RECYCLE GAS DERIVING FROM OZONIZATION

[75] Inventors: Pier P. Rossi, Garlasco; Roberto Jacuone, Cesano Maderno; Franco Magnoni, Milan, all of Italy

[73] Assignee: Snia Viscosa Societa Nazional Industria Applicazioni Viscosa sPa, Milan, Italy

[21] Appl. No.: 52,911

[22] Filed: Jun. 28, 1979

[30] Foreign Application Priority Data

Jun. 30, 1978 [IT] Italy .............................. 25159 A/78
Sep. 21, 1978 [IT] Italy .............................. 27929 A/78

[51] Int. Cl.$^3$ .................... C07D 323/02; B01D 19/00; B01D 47/00; B01D 46/00; C07C 51/16; C07C 1/20
[52] U.S. Cl. ....................................... 549/431; 55/48; 55/55; 55/89; 55/97; 568/469; 562/544; 562/545
[58] Field of Search ............... 260/338, 339; 549/431; 55/89, 97, 48, 55; 568/469; 562/544, 545

[56] References Cited

PUBLICATIONS

*Primary Examiner*—Norma S. Milestone
*Attorney, Agent, or Firm*—Hubbell, Cohen, Stiefel & Gross

[57] ABSTRACT

A process for separating and recovering organic compounds from an oxygen-containing recycle gas deriving from an ozonization process is disclosed. The process comprises the separation of products in form of fumes from the gas, the countercurrent scrubbing of the gas with a polyoxyalkyleneglycol containing 2-4 carbon atoms, pre-treated with a monocarboxylic acid anhydride and/or the countercurrent scrubbing of the gas with the polyoxyalkyleneglycol or with an excess of a base. The organic compounds are recovered either by stripping (at atmospheric pressure or under vacuum) or by hydrolysis followed by distillation (at atmospheric pressure or under vacuum).

19 Claims, No Drawings

PROCESS FOR PURIFYING OXYGEN CONTAINING RECYCLE GAS DERIVING FROM OZONIZATION

BACKGROUND OF THE INVENTION

This invention relates to a process for purifying oxygen-containing recycle gas deriving from the ozonisation of mono or polyunsaturated organic compounds, such as hydrocarbons, contaminated with organic compounds. The invention also relates to a process for separating and recovering said organic compounds from said oxygen-containing gas. The invention further relates to a suitable apparatus for carrying out said separation of the organic compounds from the oxygen-containing gas, and the recovery of said organic compounds.

Further objects will be specified hereinafter.

Ozone is produced industrially by supplying energy by various methods to an oxygen-containing gas. In one of the most used methods, the gas is passed through a flat or cylindrically shaped interspace between two surfaces, one of which, generally covered by a dielectric, is subjected to a voltage of some effective KV, at a frequency of 50–3000 Hz and of a suitable wave form, whereas the other is connected to earth. One or both of these surfaces are cooled because the energy yield of the ozone formation from the oxygen is low, of the order of 10–20%, the rest being dissipated as heat.

The parameters which govern the energy yield and productivity of the ozone generators include the following:
temperature and pressure of the oxygen-containing gas;
voltage, frequency and wave form;
hydrodynamic and geometrical characteristics of the apparatus;
ozone concentration in the outlet gas;
composition of the gaseous mixture.

Of these parameters, the type and composition of the oxygen-containing gas used is very important, and in particular its humidity and the oxygen concentration.

In those cases in which relatively small ozone quantities are required, for example disinfection, drinking water and similar plants, it is generally preferred to use air in an open cycle. In this case, the air, which is taken from the outside, needs only to be filtered and carefully dried (dew point less than $-50°$ C.) before being fed to the ozone generator. The ozone-containing air is then fed to the reactor in which ozonisation is carried out, and it is then discharged to atmosphere. To be able to do this, it is necessary to remove the residual ozone by known means, and to eliminate any harmful substances which may have become absorbed during the reaction, so as to fall within the limits imposed by current regulations. This leads to a plant which is relatively simple in terms of its components, but which is of low production because of its high operating cost, the total energy consumption exceeding 20 KWh/Kg of ozone.

Where much greater quantities of ozone are required (such as in the ozonisation of organic compounds), either pure oxygen is used instead of the air, or a gas mixture having an oxygen content exceeding 20% by volume, and preferably exceeding 50% by volume, which, other conditions being equal, gives a productivity and yield which is more than doubled, and consequently ozone at approximately half the cost of that obtained using air. However, this assumes the nearly complete overall recovery of the gas, as the ozone is produced in a concentration of the order of 10–50 g/Nm$^3$, and thus determines the need to operate in closed cycle. However, a further drawback arises when operating in closed cycle if the gas fed to the ozone generator contains organic substances (as in the case of gas deriving from the ozonisation of unsaturated hydrocarbons in the presence of organic acids and/or organic acid anhydrides) as these organic impurities increase during recycling, so leading to a reduction in the productivity of the ozone generator until it ceases to produce when the organic compound content is about 1% by volume.

Moreover, depending on the type of organic compounds concerned, further drawbacks can arise even if these compounds are present only in quantities of a few parts per million, these drawbacks including:
condensation and formation of deposits on the electrodes;
corrosion or alteration of the electrode surface;
formation of other harmful, dangerous or otherwise undesirable chemical compounds on discharge;
formation of explosive mixtures.

Manufacturers of ozone generating apparatus generally stipulate a maximum limit to the organic residue content of the gas, which is of the order of approximately 5–15 parts per million by volume.

Consequently, in chemical ozonisation processes in which (a) large ozone flow rate are required, and thus it is necessary to operate with gas in closed cycle in order to reduce the ozone cost, and in which (b) this gas comes into contact with organic substances in the reactor, the problem of purifying the gas with respect to the organic compounds arises. This problem has to be viewed from two aspects:
(A) the opportunity to recover the entrained organic compounds, which are often of considerable quantity and/or value. In this respect, in this type of reaction very high gas flow rates are generally present because of the low ozone concentration, and in the contact reactor this gas comes into liquid-vapour equilibrium with the mixture contained in the reactor;
(B) the need to finally obtain a gas in which the organic compounds are practically absent, and in any case less than 15 parts per million by volume.

Even today, only a few processes use ozone in the chemical industry, due mainly to the difficulties which arise when the ozonisation gas is recycled for obvious process economy reasons.

As it has not as yet been possible to carry out processes based on absorbing organic contaminating compounds in solvent due to the fact that the solvent has its own vapour pressure and would therefore contaminate the gas, one of the known methods used industrially consists of passing the gas after ozonisation over a catalyst consisting of Mn, Cr or Cu oxides absorbed in alumina, in which the organic contaminating substances are subjected to combustion at the expense of the oxygen contained in the gas. However, this process has the following drawbacks:
it does not allow recovery of the organic contaminating compounds, which are converted to carbon dioxide and water;
it requires a considerable quantity of heat exchange between two gas streams, of which the stream containing the organic compounds is heated by the sensible heat of the gas after combustion. The temperature to which the gas is raised is generally around 400° C.;

after treatment, the gas has to be bled off to keep the carbon dioxide content constant, and dried to remove the water formed in order to return the dew point of the gas to below −50° C.;

the combustion of the organic substances is not total, so that certain of the drawbacks connected with the recycling of impure gas arise.

SUMMARY OF THE INVENTION

The Applicant has now surprisingly discovered a method by which it is possible to eliminate the organic compounds present in oxygen-containing recycle gas from ozonisation of mono or polyunsaturated hydrocarbons (or other organic compounds) in the presence or absence or solvents, by treating said gas with a special solvent system which will be defined hereinafter, then possibly recovering said organic compounds, and which does not have the aforesaid drawbacks of known processes.

The present invention therefore provides a process for separating and recovering organic compounds from oxygen-containing recycle gas deriving from the ozonisation of mono or polyunsaturated organic compounds, in the presence or absence of solvents, wherein said gas, before recycling, is subjected to the following treatments in the stage order as indicated:

(a) passage through a suitable apparatus in which the products contained in the gas in the form of fumes are separated, in particular peroxide products (these products, which are soluble in the organic acids and anhydrides contained in the gas and present on the filter element in the form of condensate can be recovered in this manner and recycled through the process);

(b) countercurrent scrubbing with a polyoxyalkyleneglycol having a molecular weight of 200 to 10,000 and pretreated with an anhydride of a monocarboxylic acid containing 2 to 4 carbon atoms (hereinafter known as PAG I for simplicity); and/or (c) countercurrent scrubbing with a polyoxyalkyleneglycol having a molecular weight of 200 to about 10,000 (hereinafter known as PAG II for simplicity) or with an excess of a basic compound of an alkali metal in the form of an aqueous solution having a pH$\geq$8 (hereinafter known as solution X), the organic compounds absorbed during treatment (b) being then recovered by stripping at atmospheric pressure or under vacuum, whereas if only treatment (c) with PAG II is carried out, said compounds are subsequently recovered either by stripping at atmospheric pressure or under vacuum, or by hydrolysis followed by distillation at atmospheric pressure or under vacuum.

DESCRIPTION OF THE PREFERRED EMBODIMENTS

The hydrolysis (if using PAG II) is carried out by conventional known methods, preferably by treating the solution downstream of stage (c) under pressure at a suitable temperature and for a period exceeding some hours with a strong excees of water over the stoichiometric, for example more than ten times the stoichiometric. and preferably more than 100 times. Distillation is then carried out under high vacuum, for example 2 Torr, to recover the corresponding acid.

The alkylene residue in the PAG I can obviously be the same or different to that in the PAG II.

The PAG I used in accordance with the invention stage (b) is prepared by treating polyoxyalkyleneglycol with the anhydride of the monocarboxylic acid at a temperature of 20° to 150° C. (possibly under pressure) and preferably 70° to 105° C. with a polyoxyalkyleneglycol/monocarboxylic acid anhydride molar ratio of 1:1 to 1:10, preferably 1:2 to 1:4.

According to the present invention, stage (a) can be conveniently carried out using a filter known to the art as a brink demister, or by passing the gas through at least one column filled with glass wool.

According to the invention, the gas treatment with PAG I in stage (b) is carried out at a temperature of 0° to 50° C., preferably 15° to 25° C., at a pressure of 0.1 to 10 ata, and preferably 1.0 to 1.3 ata.

Stage (c) is carried out at a temperature of 0° to 50° C., preferably 15° to 20° C. if PAG II is used, or at a temperature of 0° to 40° C., preferably 15° to 30° C., if solution X is used.

The basic compound of the alkali metal used in the solution X is preferably $K_2CO_3$, $Na_2CO_3$, KOH, or more preferably NaOH. If NaOH is used, it is used in the form of an aqueous solution having a concentration of >0.1%, and in an excess of preferably $\geq$5%.

In that embodiment of the process according to the invention in which the gas leaving treatment (b) according to the invention, and still containing about 500-100 parts per million of organic compounds, is scrubbed with solution X, an increased processing simplicity is obtained, but at the expense of the consumption of the alkaline compound, the loss of the organic compounds absorbed in solution X, and the need to dry the gas before recycling it to the ozone generator. However, there is the advantage of being able to recycle a gas having a residual organic compound content of <<<1 ppm.

The organic compounds, in particular the acetics (propionics and/or butyrics respectively) and the hydrocarbons, are recovered from the PAG I, which contains about 10–40% by weight of said compounds, by preferably distilling said PAG I downstream of stage (b) at a temperature of 50° to 200° C., possibly under vacuum, and preferably at 70° to 135° C. under a pressure of 3 to 1000 Hg absolute.

If PAG II is used in stage (c), the acetics (propionics and/or butyrics respectively) and any hydrocarbons still present can be recovered by distilling the PAG II downstream of stage (c) under vacuum. This distillation is carried out preferably under the same conditions as indicated heretofore for the PAG I. However, in this case recovery is only partial because the PAG II is partly acetylated (propylated and butylated respectively), and hence, in order to be able to recycle it, it is necessary firstly to saponify it with water under pressure and then separate the corresponding released acid by distillation.

The process according to the invention is particularly suitable for use in the ozonisation of mono or polyunsaturated compounds, in particular hydrocarbons such as mono or polyunsaturated cycloolefines, for example cyclooctadiene, cyclodecadiene, cyclododecadiene or cyclododecatriene, or unsaturated carboxylic acids such as oleic acid etc., in the presence of solvents such as other hydrocarbons and/or organic acids and/or organic anhydrides, in particular vaseline oil and/or acetic, propionic and/or butyric acid and anhydride, and of peroxide products present also in the form of fumes.

The gas deriving from ozonisation of this type and saturated with these organic compounds can be processed to such a degree of purity by the process according to the invention as to be able to by recycled to the ozone generator without having first to be subjected to any other type of treatment, except for drying if only treatment (c) is carried out with an aqueous alkaline solution.

For this purpose, the organic compounds, separated from the recycle gas by treatment with PAG I or PAG II (if using PAG II in stage (c)), are recovered by distilling PAG I or PAG II downstream of stage (b) or stage (c) respectively (carried out preferably at a temperature of 50° to 200°).

The process according to the invention makes it possible to treat large quantities of gas with small quantities of PAG I and PAG II liquid (or solution X), therefore attaining low stripping costs.

The apparatus for carrying out the process according to the invention can in principle by any multi-stage countercurrent gas-liquid contact apparatus known to the art (e.g. perforated plate, bubble cap or valve columns).

However, in practice:
because of the very high gas throughputs, the pressure drops on the gas side should be minimised to reduce costs, and because of this it is generally not convenient to use apparatus requiring heads of liquid to be traversed (for example plate columns of any type)
because of the very small throughputs of liquid in contact with large throughputs of gas, it is at the same time advantageous to ensure good contact efficiency. For this reason, it is unadvisable to use packed columns, in which it would be impossible to completely wet the packing.

In spite of what has been previously stated, if plates were used the efficiency with respect to a theoretical stage would be low.

According to the present invention, the applicant has now discovered that those stage scrubbers in which the liquid is recycled about itself within each individual stage, such as scrubbers known to the art by the name of FELD or multi-stage fluidised bed or tunnel scrubbers etc., do not give rise to the aforesaid drawbacks.

A further object of the present invention is therefore the use of FELD scrubbers for carrying out the aforesaid treatment (stages (b) and (c)) in purifying oxygen-containing gas contaminated with organic substances and deriving from the ozonisation of mono or polyunsaturated compounds.

It is apparent that the applicant does not limit himself to this type of apparatus as the desired effect is obtainable by using different methods for recycling the liquid within a stage (e.g. tunnel scrubbers in which the liquid is recycled about itself by means of a pump, i.e. scrubbers in which the liquid is recycled about itself within the same gas contact stage.

The following examples are given by way of example, but without limiting the scope of the present invention. The degrees are degrees centigrade.

EXAMPLE 1

A scrubber (A) of conventional type, having a diameter of 350 mm and provided with a number of plates corresponding to four theoretical stages, is fed continuously at its base with a gas mixture from an ozonisation reactor, at a temperature of 10° C. and a pressure of 0.005 atg, after passing through a filter (known as a BRINK DEMISTER) in which the products present in the form of fumes have been removed (and returned to the said reactor). This gas mixture has the following compositions:

| 32 | $Nm^3/h$ | $O_2$ |
|---|---|---|
| 32 | $Nm^3/h$ | $CO_2$ |
| 1.13 | Kg/h | acetic acid |
| 0.47 | Kg/h | acetic anhydride |
| 0.007 | Kg/h | cyclododecatriene (CDT) |

6.5 Kg/h of an acetylated polyoxyethyleneglycol (kept at a temperature of 10° C.) of average molecular weight 387 and containing 3% by weight of acetic acid+acetic anhydride (in a weight ratio of 1:1.6) and 0.07% CDT is fed into the top of the scrubber (A).

8.11 Kg/h of a mixture containing 22.2% by weight of acetic acid and acetic anhydride together (in a weight ratio of 2.04:1) and 0.142% CDT are discharged from the base of the scrubber (A), and a gas flows from the top of the scrubber (A) containing 300 p.p.m. by volume of acetic acid+acetic anhydride (expressed as acetic acid) and less than 0.1 p.p.m. of CDT, together with 0.2 p.p.m. of acetylated polyoxyethyleneglycol (entrained by the gas).

The gas leaving the scrubber (A) is fed at a temperature of 10° C. and a pressure of 0.004 atg. to the base of a conventional scrubber (B) provided with a number of plates corresponding to two theoretical stages, and 3 Kg/h of a 4% aqueous solution of NaOH is fed to the top of said scrubber (B) at a temerature of 10° C.

A solution collects at the base of the scrubber (B) containing:

| 0.11 | Kg/h | NaOH |
|---|---|---|
| 0.08 | Kg/h | sodium acetate |
| 2.62 | Kg/h | $H_2O$ | together with 0.007 p.p.m. CDT and 100 p.p.m. of acetylated polyoxyethyleneglycol. A gas saturated with moisture and containing less than 0.1 p.p.m. CDT leaves the top of scrubber (B) at a temperature of 10° C. and a pressure of 0.003 atg. This gas—free from acetic acid, acetic anhydride and acetylated polyoxyethyleneglycol—is compressed and dried to a dewpoint of −50° C., and then recycled to the ozone generator.

The polyoxyethyleneglycol mixture from scrubber (A) is fed to a distillation unit and distilled under vacuum (pressure 11 Torr) at a temperrature of 115°. In this manner the following are recovered:

| 1.04 | Kg/h | acetic acid |
|---|---|---|
| 0.43 | Kg/h | acetic anhydride |
| 0.007 | Kg/h | CDT |

The acetylated polyoxyethyleneglycol used here is prepared in the following manner: 30 kg of PEG 300 are fed at 100° C., and maintained at this temperature, into a 100 liter reactor fitted with a stirrer, thermometer, separator funnel, condenser and off gas pipe. 30 kg of acetic anhydride (purity 95%, the rest acetic acid) are fed gradually over a time of two hours under stirring. After this addition, the mixture is maintained at 100° for 30 minutes, then cooled to 75° and distilled under vacuum to give 20.38 kg of distillate having a composition of

| | | |
|---|---|---|
| 63.7% | acetic acid | |
| 36% | acetic anhydride | |
| 0.3% | by-products | |

The residue (39.6 kg) consists essentially of acetylated polyoxyethyleneglycol (containing about 3% of free acetic acid + anhydride in a weight ratio of 1:1.6)

EXAMPLE 2

The process is carried out under the same conditions and in an analogous manner to that indicated in Example 1, with the difference that the gas from scrubber (A) is fed to the base of a scrubber (B) provided with a number of plates corresponding to four theoretical stages, and 3 kg/h of polyoxyethyleneglycol of molecular weight 300 containing 0.1% of free acetic acid is fed to the top of the scrubber (B), the gas leaving the top of said scrubber (through a demister or another entrainment separator) containing 10 p.p.m. by volume of acetic acid + acetic anhydride.

The polyoxyethylenglycol solution discharged from the base of scrubber (B) contains 2% of acetic acid + acetic anhydride (free and/or bonded, expressed as acetic acid). 30 kg of said solution are fed together with 70 kg of $H_2O$ to a 150 liter autoclave fitted with a stirrer, thermometer and reflux condenser.

After heating the mixture to 105° C. for 20 hours, 0.6 Kg of acetic acid + 69.9 Kg of water are distilled off under a vacuum of 2 Torr. The residue consists of 29.4 Kg of polyoxyethyleneglycol (containing 0.1% of acetic acid) ready for recycling to scrubber (B).

EXAMPLE 3

A scrubber (A) of conventional type, having a diameter of 350 mm and provided with a number of plates corresponding to four theoretical stages, is fed continuously at its base with a gaseous mixture deriving from an ozonisation reactor, at a temperature of 23° C., and a pressure of 0.05 atg, after passing through a filter (known as a BRINK DEMISTER) in which the products present in the form of fumes have been removed (and returned to the said reactor). This gaseous mixture has the following composition:

| | | |
|---|---|---|
| 32 | $Nm^3/h$ | $O_2$ |
| 32 | $Nm^3/h$ | $CO_2$ |
| 1.91 | Kg/h | acetic acid |
| 1.12 | Kg/h | acetic anhydride |
| 0.013 | Kg/h | cyclododecatriene (CDT) |

6.5 Kg/h of an acetylated polyoxyethyleneglycol (maintained at a temperature of 23° C.) of average molecular weight 387 and containing 3% by weight of acetic acid + acetic anhydride (in a weight ratio of 1:1.6) and 0.07% CDT are fed to the top of scrubber (A).

9.18 Kg/h of a mixture is discharged from the base of scrubber (A) containing 29% by weight of acetic acid and acetic anhydride together (in a ratio of 1.5:1) and 0.19% CDT, and a gas flows from the top of scrubber (A) containing 1500 p.p.m. by volume of acetic acid + acetic anhydride (expressed as acetic acid) and less than 0.2 p.p.m. of CDT, together with 0.2 p.p.m. of acetylated polyoxyethyleneglycol (entrained by the gas).

The gas leaving scrubber (A) is fed at a temperature of 23° C. and a pressure of 0.048 atg to the base of a conventional scrubber (B) provided with a number of plates corresponding to two theoretical stages, and 6 Kg/h of a 5% aqueous NaOH solution of temperature 23° C. are fed to the top of said scrubber (B).

A solution collects at the base of scrubber (B) containing:

| | | |
|---|---|---|
| 0.076 | Kg/h | NaOH |
| 0.46 | Kg/h | sodium acetate |
| 4.60 | Kg/h | $H_2O$ | together with <0.1 p.p.m. CDT and about 100 p.p.m. acetylated polyoxyethyleneglycol. A gas saturated with moisture and containing less than 0.2 p.p.m. CDT flows from the top of scrubber (B) at a temperature of 10° C. and a pressure of 0.046 atg. This gas—free from acetic acid, acetic anhydride and acetylated polyoxyethyleneglycol—is compressed and dried to a dew point of −50° C., and recycled to the ozone generator. The polyoxyethyleneglycol mixture leaving scrubber (A) is fed into a distillation unit and distilled under vacuum (pressure 11 Torr) at a temperature of 115°. In this manner the following are recovered:

| | | |
|---|---|---|
| 1.43 | Kg/h | acetic acid |
| 0.90 | Kg/h | acetic anhydride |
| 0.013 | Kg/h | CDT |

The acetylated polyoxyethyleneglycol used here is prepared in the manner described in Example 1.

EXAMPLE 4

The process is carried out under the same conditions and in the same manner as described in Example 3, with the difference that the gas leaving scrubber (A) is fed to the base of a scrubber (B) provided with a number of theoretical plates corresponding to four theoretical stages, and 5.11 Kg/h of polyoxyethyleneglycol of molecular weight 300 containing 0.1% of free acetic acid are fed to the top of said scrubber (B), the gas flowing from the top of said scrubber containing 10 p.p.m. by volume of acetic acid + acetic anhydride after passing through a demister or another entrainment separator.

The polyoxyethyleneglycol solution discharged from the base of scrubber (B) contains 5.75% of acetic acid + acetic anhydride (free and/or bonded, expressed as acetic acid).

30 Kg of said solution are fed together with 70 Kg $H_2O$ to a 150 liter autoclave fitted with a stirrer, thermometer and reflux condenser. After heating the mixture to 105° C. for 20 hours, 1.72 Kg of acetic acid + 69.9 Kg of water are distilled off under a vacuum of 2 Torr. The residue consists of 28.25 Kg of polyoxyethyleneglycol (containing 0.1% of acetic acid) ready for recycling to scrubber (B).

EXAMPLE 5

A scrubber (A) of conventional type, having a diameter of 350 mm and provided with a number of plates corresponding to four theoretical stages, is fed continuously at its base with a gaseous mixture deriving from an ozonisation reactor at a temperature of 20° C. and a pressure of 0.08 atg, after passing through a filter (known as a BRINK DEMISTER) in which the products present in the form of fumes have been removed (and returned to the said reactor). This gas mixture has the following composition:

| | | |
|---|---|---|
| 35 | Nm³/h | O₂ |
| 35 | Nm³/h | CO₂ |
| 1.93 | Kg/h | acetic acid |
| 1.41 | Kg/h | acetic anhydride |
| 0.03 | Kg/h | cyclododecatriene (CDT) |

10 Kg/h of an acetylated polyoxypropyleneglycol (maintained at a temperature of 20° C.) of average molecular weight 1084 and containing 2% by weight of acetic acid+acetic anhydride (in a weight ratio of 1:1.6) and 0.05% CDT are fed to the top of scrubber (A).

13.2 Kg/h of a mixture is discharged from the base of scrubber (A) containing 25.5% by weight of acetic acid and acetic anhydride together (in a weight ratio of 1.31:1) and 0.26% CDT, and a gas flows from the top of scrubber (A) containing 700 p.p.m. by volume of acetic anhydride+acetic acid (expressed as acetic acid) and less than 0.2 p.p.m. of CDT, together with 0.2 p.p.m. of acetylated polyoxypropyleneglycol (entrained by the gas).

The gas leaving scrubber (A) is fed at a temperature of 20° C. and a pressure of 0.077 atg. to the base of a conventional scrubber (B) provided with a number of plates corresponding to two theoretical stages, and 5 Kg/h of a 4.5% aqueous NaOH solution of temperature 20° C. are fed to the top of said scrubber (B).

A solution is collected at the base of scrubber (B) containing:

| | | |
|---|---|---|
| 0.106 | Kg/h | NaOH |
| 0.243 | Kg/h | sodium acetate |
| 3.56 | Kg/h | H₂O | and <0.2 p.p.m. CDT together with 80 p.p.m. of acetylated polyoxypropyleneglycol. A gas saturated with moisture and containing less than 0.1 p.p.m. CDT flows from the top of scrubber (B) at a temperature of 20° C. and a pressure of 0.077 atg. This gas—free from acetic acid, acetic anhydride and acetylated polyoxypropyleneglycol—is compressed and dried to a dew point of −50° C., then recycled to the ozone generator.

The polyoxypropyleneglycol mixture leaving scrubber (A) is fed into a distillation unit and distilled under vacuum (pressure 20 Torr) at a temperature of 115°. In this manner the following are recovered:

| | | |
|---|---|---|
| 1.83 | Kg/h | acetic acid |
| 1.34 | Kg/h | acetic anhydride |
| 0.03 | Kg/h | CDT |

The acetylated polyoxypropyleneglycol used here is prepared in the following manner: 30 Kg of PPG 1000 are fed at a temperature of 100° C., and maintained at this temperature, in a 100 liter reactor fitted with a stirrer, thermometer, separator funnel, condenser and offgas pipe. 10 Kg of acetic anhydride (purity 95%, remainder acetic acid) are added gradually over a time of 2 hours while stirring. After this addition, the mixture is maintained at 100° for 30 minutes, then cooled to 75°, after which 6.4 Kg of a distillate are distilled off under vacuum, having a composition of:

| | |
|---|---|
| 54.75% | acetic acid |
| 45.0% | acetic anhydride |
| 0.25% | by-products |

The residue (33.5 Kg) consists essentially of acetylated polyoxypropyleneglycol (containing approximately 3% of free acetic acid+anhydride in a weight ratio of 1:1.6).

EXAMPLE 6

The process is carried out under the same conditions and in an analogous manner to Example 1, with the difference that the gas leaving scrubber (A) is fed to the base of a scrubber (B) provided with a number of plates corresponding to four theoretical stages, and 6 Kg/h of polyoxypropyleneglycol of molecular weight 1000 and containing 0.1% of free acetic acid are fed to the top of said scrubber (B), the gas flowing from the top of said scrubber (through a demister or another entrainment separator) containing 12 p.p.m. by volume of acetic acid+acetic anhydride.

The polyoxypropyleneglycol solution discharged from the base of scrubber (B) contains 2.8% of acetic acid+acetic anhydride (free and/or bonded, expressed as acetic acid). 30 Kg of said solution are fed together with 70 Kg H₂O into a 150 liter autoclave fitted with a stirrer, thermometer and reflux condenser.

After heating the mixture to 105° C. for a time of 20 hours, 0.87 Kg of acetic acid+69.9 Kg of water are distilled off under a vacuum of 2 Torr. The residue consists of 29.1 Kg of polyoxypropyleneglycol (containing 0.1% of acetic acid) ready for recycling to scrubber (B).

EXAMPLE 7

A scrubber (A) of conventional type having a diameter of 350 mm and provided with a number of plates corresponding to four theoretical stages, is fed continuously at its base with a gaseous mixture deriving from an ozonisation reactor at a temperature of 23° C. and pressure of 0.05 atg, after passing through a filter (known as a BRINK DEMISTER) in which the products present in the form of fumes have been removed (and returned to said reactor). This gaseous mixture has the following composition:

| | | |
|---|---|---|
| 32 | Nm³/h | O₂ |
| 32 | Nm³/h | CO₂ |
| 1.91 | Kg/h | acetic acid |
| 1.12 | Kg/h | acetic anhydride |
| 0.013 | Kg/h | cyclododecatriene (CDT) |

8 Kg/h of a propionated polyoxyethleneglycol (maintained at a temperature of 23° C.) of average molecular weight 412 and containing 2.6% by weight of acetic acid+acetic anhydride (in a weight ratio of 1:1.36) and 0.07% CDT are fed to the top of scrubber (A).

10.84 Kg/h of a mixture are discharged from the base of scrubber (A) containing 28.36% by weight of acetic acid and acetic anhydride together (in a ratio of 1.57:1) and 0.175% CDT, and a gas flows from the top of scrubber (A) containing 1000 p.p.m. by volume of acetic acid+acetic anhydride (expressed as acetic acid) and less than 0.2 p.p.m. of CDT, together with 0.2 p.p.m. of propionated polyoxyethyleneglycol (entrained by the gas).

The gas leaving scrubber (A) is fed at a temperature of 23° C. and a pressure of 0.048 atg to the base of a conventional scrubber (B) provided with a number of plates corresponding to two theoretical stages, and 8 Kg/h of a 5% aqueous solution of Na$_2$CO$_3$ at a temperature of 20° C. are fed to the top of said scrubber (B).

A solution collects at the base of scrubber (B) containing:

| 0.210 | Kg/h | Na$_2$CO$_3$ |
|---|---|---|
| 0.293 | Kg/h | sodium acetate |
| 6.45 | Kg/h | H$_2$O | together with <0.2 p.p.m. CDT and about 90 p.p.m. propionated polyoxyethyleneglycol. A gas saturated with moisture and containing less than 0.2 p.p.m. CDT flows from the top of scrubber (B) at a temperature of 20° C. and a pressure of 0.046 atg. This gas—free from acetic acid, acetic anhydride and propionated polyoxyethyleneglycol—is compressed and dried to a dew point of −50° C., and then recycled to the ozone generator. The polyoxyethyleneglycol mixture leaving scrubber (A) is fed into a distillation unit and distilled under vacuum (pressure 11 Torr) at a temperature of 115°. In this manner, the following are recovered:

| 1.78 | Kg/h | acetic acid |
|---|---|---|
| 1.04 | Kg/h | acetic anhydride |
| 0.013 | Kg/h | CDT |

The propionated polyoxyethyleneglycol used here is prepared in the following manner: 30 Kg of PEG 300 are fed at a temperature of 100° C., and maintained at this temperature, into a 100 liter reactor fitted with a stirrer, thermometer, separator funnel, condenser and offgas pipe. 39.1 Kg of propionic anhydride (purity 97%, remainder propionic acid) are added gradually over a time of two hours with stirring. After the addition, the mixture is maintained at 100° for 30 minutes, then cooled to 45°, after which 26.7 Kg of a distillate are distilled off under vacuum, having a composition of

| 58.1% | propionic acid |
|---|---|
| 41.5% | propionic anhydride |
| 0.4% | by-products |

The residue (42.3 kg) consists essentially of propionated polyoxyethyleneglycol (containing about 2.6% of free propionic acid+anhydride in a weight ratio of 1:1.36).

EXAMPLE 8

The process is carried out under the same conditions and in an analogous manner to Example 7, with the difference that the gas from scrubber (A) is fed to the base of a scrubber (B) provided with a number of plates corresponding to four theoretical stages, and 4 Kg/h of polyoxyethyleneglycol of molecular weight 300 containing 0.1% of free acetic acid are fed to the top of said scrubber (B), the gas leaving the top of said scrubber through a demister or another entrainment separator containing 10 p.p.m. by volume of acetic acid+acetic anhydride.

The polyoxyethyleneglycol solution discharged from the base of scrubber (B) contains 5% of acetic acid+acetic anhydride (free and/or bonded, expressed as acetic acid).

30 Kg of said solution are fed together with 70 Kg H$_2$O into a 150 liter autoclave fitted with a stirrer, thermometer and reflux condenser. After heating the mixture to 105° C. for a time of 20 hours, 1.54 Kg of acetic acid+69.9 Kg of water are distilled off under a vacuum of 2 Torr. The residue consists of 28.7 Kg of polyoxyethyleneglycol (containing 0.1% of acetic acid) ready for recycling to the scrubber (B).

EXAMPLE 9

A scrubber (A) of conventional type, having a diameter of 350 mm and provided with a number of plates corresponding to four theoretical stages, is fed continuously at its base with a gaseous mixture deriving from an ozonisation reactor at a temperature of 12° C. and a pressure of 0.25 atg, after passing through a filter (known as a BRINK DEMISTER) in which the products present in the form of fumes have been removed (and returned to the said reactor). This gas mixture has the following composition:

| 24.4 | Nm$^3$/h | O$_2$ |
|---|---|---|
| 30 | Nm$^3$/h | CO$_2$ |
| 0.96 | Kg/h | acetic acid |
| 0.40 | Kg/h | acetic anhydride |
| 0.14 | Kg/h | cyclooctadiene (COD) |

5.5 Kg/h of an acetylated polyoxyethyleneglycol (maintained at a temperature of 12° C.) of average molecular weight 387 and containing 3% by weight of acetic acid+acetic anhydride (in a weight ratio of 1:1.6) and 0.4% COD are fed to the top of scrubber (A).

7.03 Kg/h of a mixture are discharged from the base of scrubber (A) containing 21.8% by weight of acetic acid and acetic anhydride together (in a weight ratio of 2.04:1) and 2.05% COD, and a gas leaves the top of scrubber (A) containing 300 p.p.m. by volume of acetic acid+acetic anhydride (expressed as acetic acid) and 1.3 p.p.m. of COD, together with 0.2 p.p.m. of acetylated polyoxyethyleneglycol (entrained by the gas).

The gas leaving scrubber (A) is fed at a temperature of 12° C. and a pressure of 0.245 atg to the base of a conventional scrubber (B) provided with a number of plates corresponding to two theoretical stages, and 2.55 Kg/h of a 4% aqueous NaOH solution of temperature 12° C. are fed to the top of said scrubber (B).

A solution is collected at the base of scrubber (B) containing:

| 0.093 | Kg/h | NaOH |
|---|---|---|
| 0.068 | Kg/h | sodium acetate |
| 2.27 | Kg/h | H$_2$O | together with 0.14 p.p.m. COD and 100 p.p.m. acetylated polyoxyethyleneglycol. A gas saturated with moisture and containing less than 1 p.p.m. COD flows from the top of scrubber (B) at a temperature of 12° C. and a pressure of 0.23 atg. This gas—free from acetic acid, acetic anhydride and acetylated polyoxyethyleneglycol—is compressed and dried to a dew point of −50° C., and recycled to the ozone generator.

The polyoxyethyleneglycol mixture leaving scrubber (A) is fed into a distillation unit and distilled under vacuum (pressure 11 Torr) at a temperature of 115°. In this manner the following are recovered:

| 0.88 | Kg/h | acetic acid |
|---|---|---|

| | | |
|---|---|---|
| 0.36 | Kg/h | acetic anhydride |
| 0.14 | Kg/h | COD |

The acetylated polyoxyethyleneglycol used here is prepared in a manner similar to Example 1.

EXAMPLE 10

The process is carried out under the same conditions and in an analogous manner to Example 1, with the difference that the gas leaving scrubber (A) is fed to the base of a scrubber (B) provided with a number of plates corresponding to four theoretical stages, and 2.55 Kg/h of polyoxyethyleneglycol of molecular weight 300 and containing 0.1% of free acetic acid are fed to the top of said scrubber (B), the gas leaving the top of said scrubber (through a demister or another entrainment separator) containing 10 p.p.m. by volume of acetic acid + acetic anhydride.

The polyoxyethyleneglycol solution discharged from the base of scrubber (B) contains 2% of acetic acid + acetic anhydride (free and/or bonded, expressed as acetic acid). 30 Kg of said solution are fed together with 70 Kg $H_2O$ into a 150 liter autoclave fitted with a stirrer, thermometer and reflux condenser.

After heating the mixture to 105° C. for 20 hours, 0.6 Kg of acetic acid + 69.9 Kg of water are distilled off under a vacuum of 2 Torr. The residue consists of 29.4 Kg of polyoxyethyleneglycol (containing 0.1% of acetic acid) ready for recycling to scrubber (B).

EXAMPLE 11

A scrubber (A) of conventional type, having a diameter of 350 mm and provided with a number of plates corresponding to four theoretical stages, is fed continuously at its base with a gaseous mixture deriving from an ozonisation reactor, at a temperature of 22° C. and a pressure of 0.06 atg, after passing through a filter (known as a BRINK DEMISTER) in which the products present in the form of fumes have been removed (and returned to said reactor). This gaseous mixture has the following composition:

| | | |
|---|---|---|
| 35 | $Nm^3/h$ | $O_2$ |
| 35 | $Nm^3/h$ | $CO_2$ |
| 0.301 | Kg/h | propionic acid |
| 0.184 | Kg/h | propionic anhydride |
| 0.010 | Kg/h | cyclododecatriene (CDT) |

2 Kg/h of a propionated polyoxyethyleneglycol (maintained at a temperature of 22° C.) of average molecular weight 412 and containing 0.6% by weight of propionic acid + propionic anhydride (in a weight ratio of 1:1.17) and 0.07% CDT are fed to the top of scrubber (A).

2.48 Kg/h of a mixture are discharged from the base of scrubber (A) containing 19.7% by weight of propionic acid and propionic anhydride together (in a ratio of 1.6:1) and 0.4% CDT, and a gas flows from the top of scrubber (A) containing 30 p.p.m. by volume of propionic acid + propionic anhydride (expressed as propionic acid) and less than 0.5 p.p.m. of CDT, together with 0.2 p.p.m. of propionated polyoxyethyleneglycol (entrained by the gas).

The gas leaving scrubber (A) is fed at a temperature of 23° C. and a pressure of 0.058 atg to the base of a conventional scrubber (B) provided with a number of plates corresponding to two theoretical stages, and 3 Kg/h of a 1.5% aqueous NaOH solution of temperature 23° C. are fed to the top of said scrubber (B).

A solution collects at the base of scrubber (B) containing:

| | | |
|---|---|---|
| 0.040 | Kg/h | NaOH |
| 0.009 | Kg/h | sodium propionate |
| 1.69 | Kg/h | $H_2O$ | together with <0.2 p.p.m. CDT and about 90 p.p.m. propionated polyoxyethyleneglycol. A gas saturated with moisture and containing less than 0.5 p.p.m. CDT flows from the top of scrubber (B) at a temperature of 23° C. and a pressure of 0.055 atg. This gas—free from propionic acid, propionic anhydride and propionated polyoxyethyleneglycol—is compressed and dried to a dew point of −50° C., and recycled to the ozone generator. The polyoxyethyleneglycol mixture leaving scrubber (A) is fed into a distillation unit and distilled under vacuum (pressure 12 Torr) at a temperature of 130°. In this manner the following are recovered:

| | | |
|---|---|---|
| 0.296 | Kg/h | propionic acid |
| 0.181 | Kg/h | propionic anhydride |
| 0.010 | Kg/h | CDT |

The propionated polyoxyethyleneglycol used here is prepared in the following manner: 30 Kg of P E G 300 are fed at 105° C., and maintained at that temperature, into a 100 liter reactor fitted with a stirrer, thermometer, separator funnel, condenser and offgas pipe. 40 kg of propionic anhydride (purity 97%, remainder propionic acid) are fed gradually over a time of two hours while stirring. After the addition, the mixture is kept at 105° for 30 minutes, then cooled to 65°, and 25.5 Kg of distillate are then distilled off having a composition of

| | |
|---|---|
| 59% | propionic acid |
| 40.9% | propionic anhydride |
| 0.4% | by-products |

The residue (42.4 Kg) consists essentially of propionated polyoxyethyleneglycol (containing about 3% of free propionic acid + propionic anhydride in a weight ratio of 1:1.4).

EXAMPLE 12

A scrubber (A) of conventional type having a diameter of 350 mm and provided with a number of plates corresponding to four theoretical stages is fed continuously at its base at a temperature of 22° C. and a pressure of 0.06 atg, with a gaseous mixture from an ozonisation reactor in which cyclododecatriene has been ozonised, the gas mixture having passed through a filter (known as a BRINK DEMISTER), in which the products present in the form of fumes have been removed (and returned to the said reactor). This gaseous mixture has the following composition:

| | | |
|---|---|---|
| 35 | $Nm^3/h$ | $O_2$ |
| 35 | $Nm^3/h$ | $CO_2$ |
| 0.301 | Kg/h | propionic acid |
| 0.184 | Kg/h | propionic anhydride |
| 0.010 | Kg/h | cyclododecatriene (CDT) |

4 Kg/h of an acetylated polyoxyethyleneglycol (kept at a temperature of 22° C.) of average molecular weight 300 and containing 0.1% by weight of propionic acid + propionic anhydride (in a weight ratio of 1:1.17) and 0.02% CDT are fed to the top of scrubber (A).

4.47 Kg/h of a mixture are discharged from the base of scrubber (A) containing 10.9% by weight of propionic acid and propionic anhydride together (in a weight ratio of 1.6:1) and 0.22% CDT, and a gas flows from the top of scrubber (A) containing 10 p.p.m. by volume of propionic acid + propionic anhydride (expressed as propionic acid) and less than 0.2 p.p.m. of CDT, together with 0.2 p.p.m. of acetylated polyoxyethyleneglycol (entrained by the gas).

The gas flowing from scrubber (A) is recycled to the ozone generator.

The polyoxyethyleneglycol mixture leaving scrubber (A) is fed into a distillation unit and distilled under vacuum (pressure 2 Torr) at a temperature of 130° C. In this manner, the following are recovered:

| 0.3 | Kg/h | propionic acid |
| 0.180 | Kg/h | propionic anhydride |
| 0.010 | Kg/h | CDT |

The acetylated polyoxyethyleneglycol used here is prepared in the following manner: 30 Kg of PEG 220 are fed at a temperature of 100° C., and kept at this temperature, into a 100 liter reactor provided with a stirrer, thermometer, separator funnel, condenser and offgas pipe. 40 Kg of acetic anhydride (purity 95%, remainder acetic acid) are added gradually over a time of two hours while stirring. After the addition, the mixture is maintained at 100° for 30 minutes, is then cooled to 75°, and 2.85 kg of a distillate are distilled off under vacuum, having a composition of

| 64.2% | (by weight) | acetic acid |
| 35.6% | (by weight) | acetic anhydride |
| 0.2% | (by weight) | by-products |

The residue (41.5 Kg) consists essentially of acetylated polyoxyethyleneglycol.

EXAMPLE 13

A scrubber (B) of conventional type, having a diameter of 350 mm and provided with a number of plates corresponding to three theoretical stages, is fed continuously at its base at a temperature of 35° C. and a pressure of 0.07 atg, with a gaseous mixture from an ozonisation reactor in which oleic acid is ozonised, this gaseous mixture having been passed through a filter (known as a BRINK DEMISTER) in which the products present as fumes have been removed (and returned to the said reactor). This gaseous mixture has the following composition:

| 32 | Nm³/h | $O_2$ |
| 32 | Nm³/h | $CO_2$ |
| 0.201 | Kg/h | pelargonic acid |
| <0.01 | Kg/h | other organic acids (oleic + azelaic) |

2 Kg/h of a polyoxyethyleneglycol (maintained at a temperature of 35° C.) of average molecular weight 300 are fed to the top of scrubber (B).

2.2 Kg/h of a mixture are discharged from the base of scrubber (B) containing 10.9% by weight of pelargonic acid and a small quantity (of the order of 0.05%) of the other organic acids (azelaic + oleic), and a gas flows from the top of scrubber (B) containing 8 p.p.m. by volume of organic compounds (mainly pelargonic acid).

The gas flowing from scrubber (B) is fed directly to the ozone generator. The polyoxyethyleneglycol mixture from scrubber (B) is fed into a distillation unit and distilled under vacuum (pressure 0.02 Torr) at a temperature of 130° C. In this manner 0.2 Kg/h of pelargonic acid containing a small quantity of other acids (oleic + azelaic) is recovered.

We claim:

1. A process for separating and recovering organic compounds from oxygen-containing recycle gas deriving from the ozonisation of mono or polyunsaturated compounds, in the presence or absence of solvents, wherein said gas, before being recycled to an ozone generator, is subjected to a treatment in the stage order as indicated comprising:
   (a) passage through an apparatus comprising a filter containing glass wool in which peroxide products contained in the gas in the form of fumes are separated by filtering;
   (b) countercurrent scrubbing with a polyoxyalkyleneglycol having a molecular weight of 200 to 10,000 and pretreated with an anhydride of a monocarboxylic acid containing 2 to 4 carbon atoms (PAG I); and
   (c) countercurrent scrubbing with an excess of a basic compound of an alkali metal in the form of an aqueous solution having a $pH \geq 8$;
the organic compounds absorbed during said countercurrent scrubbing in stage (b) being then recovered by stripping at atmospheric pressure or under vacuum.

2. A process according to claim 1, wherein said distillation is carried out at a temperature of 50° to 200° C.

3. A process according to claim 1, wherein the alkylene residue in the polyoxyalkyleneglycol contains 2 to 3 carbon atoms.

4. A process according to claim 1, wherein the basic compound used in the form of an aqueous solution in treatment (c) is NaOH.

5. A process as claimed in anyone of claims 1, 2, 3 or 4, wherein the pretreatment of the polyoxyalkyleneglycol with the anhydride of the monocarboxylic acid is carried out at a temperature of 20° to 150° C. and at a polyoxyalkyleneglycol/monocarboxylic acid anhydride molar ratio of 1:1 to 1:10.

6. A process according to any one of claims 1, 2, 3 or 4, wherein stage (a) is carried out by passing said gas from an ozonisation reactor through a filter known as a BRINK DEMISTER or through at least one column filled with glass wool.

7. A process according to anyone of claims 1, 2, 3 or 4, wherein the treatment in stage (b) is carried out at a temperature of 0° to 50° C., and at a pressure of 0.5 to 10 atg.

8. A process according to anyone of claims 1, 2, 3 or 4, wherein the treatment in stage (c), with said aqueous solution of said basic alkaline compound is carried out at a temperature of 0° to 40° C.

9. A process according to claim 8, wherein said treatment is carried out with an excess $\geq 5\%$ of a solution of 0.1% NaOH.

10. A process according to claim 2, wherein said distillation is carried out at a temperature of 70° to 135° C. and at a pressure of 3 to 1000 mm Hg absolute.

11. A process according to any one of claims 1, 2, 4 or 10, wherein the treatment indicated in stage (b) is carried out in a stage scrubber in which the liquid is recycled about itself within each individual stage.

12. A process according to, either claim 1 or 2 which is used for recovering organic compounds from oxygen-containing recycle gas deriving from the ozonization of mono or polyunsaturated compounds, said mono or polyunsaturated compounds being mono or polyunsaturated hydrocarbons or carboxylic acids, in the presence or absence of solvents, said solvents selected from the group consisting of vaseline oil, acetic acid, propionic acid, butyric acid, acetic anhydride, butyric anhydride and propionic anhydride.

13. A process according to claim 5, wherein said pretreatment is carried out at 70° to 105° C.

14. A process according to claim 5, wherein said pretreatment is carried out at a polyoxyalkyleneglycol/monocarboxylic acid anhydride molar ratio of 1:2 to 1:4.

15. A process according to claim 7, wherein the treatment in stage (b) is carried out at 15° to 25° C.

16. A process according to claim 7, wherein the treatment in stage (b) is carried out at a pressure of 1.0 to 1.3 atg.

17. A process according to claim 8, wherein the treatment in stage (c) is carried out at 15° to 50° C.

18. A process according to any one of claims 1, 2, 4 or 10, wherein the treatment indicated in stage (c) is carried out in a stage scrubber in which the liquid is recycled about itself within each individual stage.

19. A process according to any one of claims 1, 2, 4 or 10, wherein the treatment indicated in stage (b) and stage (c) is carried out in a stage scrubber in which the liquid is recycled about itself within each individual stage.

* * * * *